(12) United States Patent
Nakano et al.

(10) Patent No.: US 8,287,927 B2
(45) Date of Patent: Oct. 16, 2012

(54) PROCESSED PRODUCT OF FENUGREEK SEEDS AND METHOD FOR PRODUCING THE SAME

(75) Inventors: Yuki Nakano, Osaka (JP); Shohei Hoshino, Osaka (JP); Jinji Shono, Osaka (JP); Nobuaki Tsuge, Osaka (JP)

(73) Assignee: House Foods Corporation, Higashiosaka-shi (JP)

( * ) Notice: Subject to any disclaimer, the term of this patent is extended or adjusted under 35 U.S.C. 154(b) by 321 days.

(21) Appl. No.: 12/596,406

(22) PCT Filed: Apr. 17, 2008

(86) PCT No.: PCT/JP2008/057498
§ 371 (c)(1),
(2), (4) Date: Oct. 16, 2009

(87) PCT Pub. No.: WO2008/133173
PCT Pub. Date: Nov. 6, 2008

(65) Prior Publication Data
US 2010/0062091 A1    Mar. 11, 2010

(30) Foreign Application Priority Data

Apr. 17, 2007  (JP) ................................. 2007-108525
Oct. 22, 2007  (JP) ................................. 2007-274006

(51) Int. Cl.
*A61K 36/00* (2006.01)
(52) U.S. Cl. ..................... 424/776; 424/94.61; 424/725; 435/201
(58) Field of Classification Search ........................ None
See application file for complete search history.

(56) References Cited

U.S. PATENT DOCUMENTS 3,620,919 A * 11/1971 Hardman ..................... 435/267
6,013,289 A    1/2000 Blank et al.

FOREIGN PATENT DOCUMENTS

| JP | 11-69953 A | 3/1999 |
| JP | 2000-3294 A | 2/2000 |
| JP | 2005-341801 A | 12/2005 |
| JP | 2007-269685 A | 10/2007 |

OTHER PUBLICATIONS

Elujoba (FITOTERAPIA, vol. 56, No. 6, 1985, pp. 368-370).*
Taylor (J. Agric. Food Chem. (2000), vol. 48, pp. 5206-5210).*
Randhir, Reena et al., "Improved α-amylase and *Helicobacter pylori* inhibition by fenugreek extracts derived via solid-state bioconversion using *Rhizopus oligosporus*", Asia Pacific Journal of Clinical Nutrition, 2007, vol. 16, No. 3, pp. 382-392.
Taku Uemura et al., "Prevention of diabetes with obesity with the use of fenugreek having reduced bitter taste", The Japanese Society of Nutrition and Food Science Taikai Koen Yoshishu, Apr. 20, 2007, vol. 61, p. 159.
Yuki Nakano et al., "Production of fenugreek having reduced bitter taste and confirmation of effects of preventing diabetes", Abstracts of Annual Meeting of Japan Society for Spice Research, 2007, vol. 22, pp. 23-24.
Elujoba, A.A. et al., "Saponin-Hydrolyzing Enzymes From Fenugreek Seed", FITOTERAPIA, vol. 58, No. 3, 1987, pp. 197-199.
Elujoba, A.A. et al., "Fermentation of Powdered Fenugreek Seeds for Increased Sapogenin Yields", FITOTERAPIA, vol. 56, No. 6, 1985, pp. 368-370, Table 1.
Madar Zecharia, "Fenugreek (*Trigonella* Poenumgraecum) As a Means of Reducing Postprandial Glucose Level in Diabetic Rats", Nutrition Reports International, Jun. 1984, vol. 29, No. 6, pp. 1267-1273.
Noriya Masamura et al., "Regarding bitter components in fenugreek (*Trigonella foenum-graecum* L.) seeds", Abstracts of Annual Meeting of Japan Society for Spice Research, 1999, vol. 14, pp. 22-23.
McAnuff-Harding Marie A. et al., Intestinal disaccharidases and some renal enzymes in streptozotocin-induced diabetic rats fed sapogenin extract from bitter yam (*Dioscorea polygonoides*) Life Sciences, 2006, vol. 78, No. 22, p. 2595-2600.
"Fenugreek having reduced bitter taste , confirmed to have effects of preventing diabetes and improving glycolipid metabolism in the metabolic syndrome", Presentation in the 61st Annual Meeting of Japanese Society of Nutrition and Food Science, May 17, 2007.
English Translation of p. 6/8 of PCT Request regarding disclosures made on Apr. 20, 2007, Sep. 22, 2007, and May 17, 2007.
Chen et al., "Potential of Agricultural Residues and Hay for Bioethanol Production", Applied Biochemistry and Biotechnology, vol. 142, pp. 276-290, (2007).
Japanese Office Action dated Aug. 14, 2012 for Japanese Application No. 2007-274006.

* cited by examiner

*Primary Examiner* — Susan Hoffman
(74) *Attorney, Agent, or Firm* — Birch, Stewart, Kolasch & Birch, LLP

(57) ABSTRACT

It is an object of the present invention to enhance the α-amylase inhibitory activity of a fenugreek seed component. According to the present invention, the bitter taste of fenugreek seeds can be collaterally reduced.
The present invention relates to a processed product of fenugreek seeds obtained by allowing β-glucosidase to act on a fenugreek seed-derived material and the like, and the method for producing the same.

4 Claims, 12 Drawing Sheets

```
Quantification results
CH PKNO   TIME        AREA      HEIGHT    MK  IDNO   CONC         NAME
 1    6  13.232       26879      1698                 100

TOTAL        26879      1698                 100
```

\*\*Quantification results\*\*
| CH | PKNO | TIME | AREA | HEIGHT | MK | IDNO | CONC | NAME |
|---|---|---|---|---|---|---|---|---|
| 1 | 7 | 13.182 | 50491 | 3067 | | | 100 | |
| | | TOTAL | 50491 | 3067 | | | 100 | |

```
Quantification results
CH PKNO   TIME      AREA      HEIGHT    MK   IDNO   CONC        NAME
1    6   13.232    26879      1698                  100

TOTAL     26879      1698                  100
```

PROCESSED PRODUCT OF FENUGREEK SEEDS AND METHOD FOR PRODUCING THE SAME

TECHNICAL FIELD

The present invention relates to a processed product of fenugreek seeds having enhanced α-amylase inhibitory activity and a method for producing the same.

Further, the present invention relates to a processed product of fenugreek seeds having an appetizing flavor, in which the strong bitter taste peculiar to fenugreek seeds is collaterally reduced, and a method for producing the same.

BACKGROUND ART

α-amylase is an enzyme capable of hydrolyzing starch into saccharides in vivo. If the activity of α-amylase can be suppressed, in vivo absorption of saccharides can be suppressed. Therefore, α-amylase inhibitors can be useful as effective components for food materials, tablets, and the like for diet and anti-diabetes purposes.

Fenugreek is an annual leguminous plant. Fenugreek seeds are known to have been used for long time for traditional spices such as curry powder.

Non-Patent Document 1 discloses an in vitro experiment using an extract extracted from a fenugreek powder with 30% ethanol. In the experiment, it was confirmed that such extract has an α-amylase inhibitory activity. However, the α-amylase inhibitory activity of the fenugreek powder described in Non-Patent Document 1 was not at a satisfactory level.

Meanwhile, Non-Patent Document 2 describes that when fenugreek saponin is ingested by a dog, saponin is decomposed into aglycon in the digestive tract so as to be excreted, and that when saponin is treated with β-glucosidase, a saccharide at position 26, but not a saccharide at position 3, is released from saponin. However, Non-Patent Document 2 does not describe any α-amylase inhibitory activity.

Non-Patent Document 1: Mol Cell Biochem. 2006 January; 281(1-2):173-83. Biochemical study of the anti-diabetic action of the Egyptian plants Fenugreek and Balanites Non-Patent Document 2: Lipids. 1991 March; 26(3):191-7. Implication of steroid saponins and sapogenins in the hypocholesterolemic effect of fenugreek

DISCLOSURE OF THE INVENTION

Problem to be Solved by the Invention

It is an object of the present invention to enhance the α-amylase inhibitory activity of a fenugreek seed component.

Means for Solving Problem

The present inventors have made the surprising finding that a processed product of fenugreek seeds obtained by allowing β-glucosidase to act on a fenugreek seed-derived material has α-amylase inhibitory activity that is significantly higher than that of an untreated material and has a suppressed bitter taste. This has led to the completion of the present invention. The present invention encompasses the following inventions.

(1) A processed product of fenugreek seeds obtained by allowing β-glucosidase to act on fenugreek seeds or a fenugreek seed-derived material.

(2) The processed product of fenugreek seeds according to (1), wherein the β-glucosidase is derived from a microorganism.

(3) The processed product of fenugreek seeds according to (1) or (2), wherein an enzyme preparation containing β-glucosidase is used as the β-glucosidase.

(4) The processed product of fenugreek seeds according to (3), wherein the enzyme preparation contains a polysaccharase.

(5) The processed product of fenugreek seeds according to any one of (1) to (4), wherein the fenugreek seed-derived material comprises at least one member selected from the group consisting of fenugreek seed powders, paste-like products prepared from fenugreek seeds, and fenugreek seed extracts.

(6) A pharmaceutical composition for α-amylase inhibition, which comprises the processed product of fenugreek seeds according to any one of (1) to (5) as an active ingredient.

(7) A food composition containing the processed product of fenugreek seeds according to any one of (1) to (5).

(8) A method for producing a processed product of fenugreek seeds, comprising the following steps:

a paste forming step of adding water to a fenugreek seed powder and mixing the resultant for paste forming, or grinding fenugreek seeds or a product thereof that has been steamed or boiled with water for paste forming;

an enzyme addition step of adding β-glucosidase to a paste-like product obtained in the paste forming step or a raw material used in the paste forming step, and mixing the resultant; and an enzyme reaction step of causing an enzyme reaction to proceed in the mixture obtained through the paste forming step and the enzyme addition step.

(9) The method according to (8), further comprising a drying step.

(10) A method for producing a processed product of fenugreek seeds, comprising the following steps:

a paste forming step of adding water to which β-glucosidase has been added and mixed therewith to a fenugreek seed powder and mixing the resultant for paste forming, or grinding fenugreek seeds or a product thereof that has been steamed or boiled with water to which β-glucosidase has been added and mixed therewith for paste forming; and an enzyme reaction step of causing an enzyme reaction to proceed in the mixture obtained in the paste forming step.

(11) The method according to (10), further comprising a drying step.

(12) A method for producing a processed product of fenugreek seeds, comprising the following steps:

an extraction step of obtaining an extract from fenugreek seeds or a powder thereof by extraction using a solvent;

an enzyme addition step of adding β-glucosidase to the extract and mixing the resultant; and an enzyme reaction step of causing an enzyme reaction to proceed in the mixture obtained in the enzyme addition step.

(13) The method according to (12), further comprising a drying step.

(14) An α-amylase inhibitor containing the processed product of fenugreek seeds according to any one of (1) to (5) as an active ingredient.

(15) The processed product of fenugreek seeds according to any one of (1) to (5), which is used for in vivo or in vitro inhibition of α-amylase.

(16) The processed product of fenugreek seeds according to any one of (1) to (5), which is used for prevention or treatment of a disease that can be improved by inhibition of α-amylase.

(17) A pharmaceutical composition containing the processed product of fenugreek seeds according to any one of (1) to (5) as an active ingredient, which may further contain a pharmaceutically acceptable carrier, an additive, and/or an excipient.

(18) A food composition containing the processed product of fenugreek seeds according to any one of (1) to (5) as an active ingredient, which may further contain a material acceptable as a food.

(19) A method for inhibiting α-amylase comprising the step of adding the processed product of fenugreek seeds according to any one of (1) to (5) to α-amylase.

(20) A method for preventing or treating a disease that can be improved by inhibition of α-amylase, comprising a step of administering an effective dose of the processed product of fenugreek seeds according to any one of (1) to (5) to a subject in need thereof. The subject includes mammals such as humans.

(21) The method according to (20), wherein the disease is diabetes or obesity.

Effects of the Invention

A processed product of fenugreek seeds having enhanced α-amylase-inhibitory effects can be obtained by subjecting fenugreek seeds to enzyme treatment using β-glucosidase. When such processed product is used for a medicine, food, beverage, or the like, it can be expected to obtain α-amylase-inhibitory effects with the addition of such product in an amount smaller than that used in the case of using untreated fenugreek seeds. In addition, the bitter taste peculiar to fenugreek seeds can be reduced. Further, the above processed product can be readily ingested because the amounts of components such as 4-hydroxyisoleucine (hereinafter described as 4-OH-isoleucine) therein and the flavor thereof are less likely to be changed. Therefore, the processed product of fenugreek seeds of the present invention can inhibit the in vivo action of α-amylase to degrade starch into saccharides. Accordingly, the product can be used for pharmaceutical compositions, food compositions, food materials, tablets, and the like for diet and anti-diabetes purposes.

This description includes part or all of the contents as disclosed in the descriptions and/or drawings of Japanese Patent Application Nos. 2007-274006 and 2007-108525, which are priority documents of the present application.

BEST MODE FOR CARRYING OUT THE INVENTION

1. Fenugreek Seeds

Figure 1:
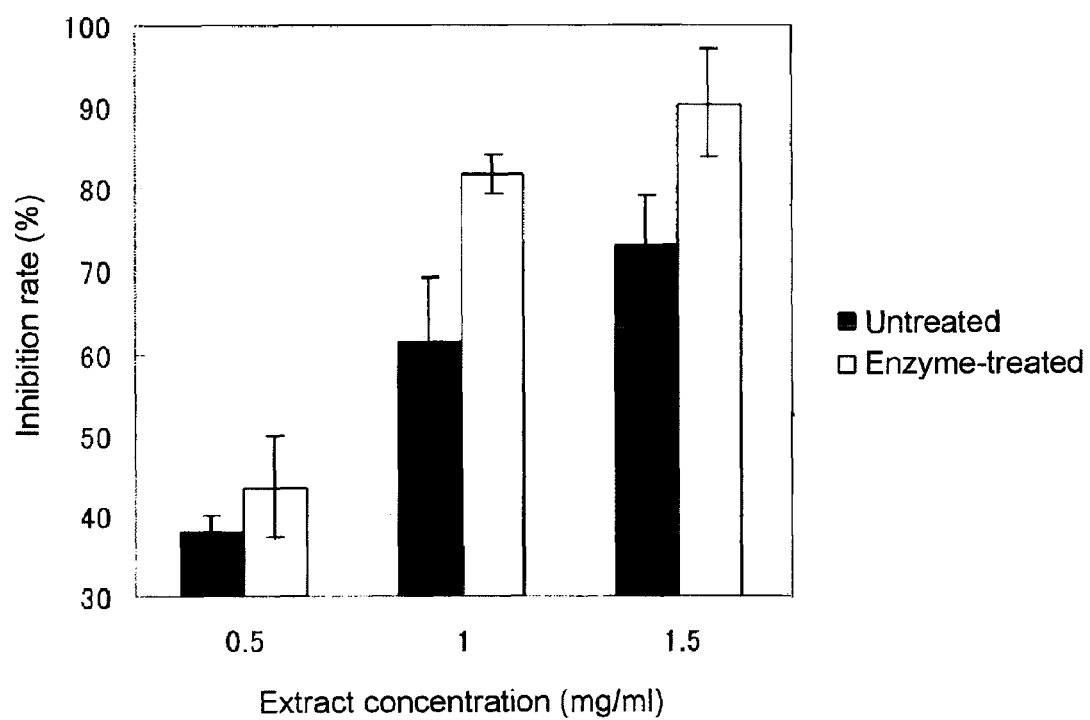
FIG. 1 is a chart showing the relationship between concentrations of extracts extracted from fenugreek seeds treated with SPEZYME CP and α-amylase activity inhibition rates.

Examples of fenugreek that can be used in the present invention include untreated fenugreek seeds, whole grains obtained by pulverizing fenugreek seeds, and a powder of specific portions such as seed endosperms and seed coats.

The term "fenugreek seeds" used herein includes not only ungerminated seeds but also germinated seeds.

The moisture content in fenugreek seeds to be used is not particularly limited. However, it is preferably approximately 8% to 12% by mass and most preferably approximately 10% by mass.

2. Fenugreek Seed-Derived Materials

In the present invention, "fenugreek seed-derived materials" are not particularly limited. However, typical examples thereof include fenugreek seed powders, paste-like products prepared with fenugreek seeds, and extracts extracted from fenugreek seeds.

Fenugreek seed powders are not particularly limited in terms of, for example, particle sizes and forms as long as such powders can be obtained by pulverizing the seeds. A pulverization means is not particularly limited. For example, pulverization can be carried out with a roll mill or the like. In addition, fenugreek seed powders, including powders of specific portions such as seed endosperms and seed coats, may be used. The moisture content of a fenugreek seed powder to be used is not particularly limited. However, it is preferably approximately 8% to 12% by mass and most preferably approximately 10% by mass.

A "paste-like product prepared with fenugreek seeds" can be prepared by two typical methods. The first method is a method for preparing a paste-like product with a fenugreek seed powder. The second method is a method for preparing a paste-like product with fenugreek seeds or a product thereof that has been steamed or boiled.

In the first method for preparing a paste-like product, a paste-like product is obtained by adding water to the above fenugreek seed powder and mixing the resultant. In such case, it is possible to carry out a β-glucosidase enzyme reaction described below in an effective manner with the addition of water. The amount of water added is not particularly limited. However, it is one or more times, preferably 1 to 20 times, and more preferably 3 to 10 times, as great as the weight of the fenugreek seed powder. If the amount of water added is insufficient, the viscosity increases excessively. This might make it difficult to obtain a uniform paste-like product. On the other hand, if the amount of water added is excessive, the time for drying is prolonged. This might cause reduction in working efficiency and this might not be preferable in terms of cost. In addition, preferably, the thus obtained paste-like product is subjected to heating treatment prior to the addition of an enzyme such as β-glucosidase. This is because such heating treatment results in sterilization, deactivation of enzymes such as lipoxygenase causing generation of a grassy smell and protease that degrades a protein, and ease of elution of components from tissue, such that an enzyme reaction of β-glucosidase or the like can be smoothly carried out. Preferably, heating is carried out at 100° C. for approximately 5 minutes.

In the second method for preparing a paste-like product, a paste-like product is obtained by grinding fenugreek seeds or a product thereof that has been steamed or boiled with water. A "product that has been steamed or boiled" can be obtained herein by boiling and/or steaming seeds. A typical example of the method is described below. First, fenugreek seeds are added to boiling water (boiling water in an amount that is, for example, at least 3 times, preferably 3 to 20 times, and more preferably 3 to 10 times as great as the weight of the fenugreek seeds), followed by heating treatment for approximately 5 minutes. Such heating results in sterilization and deactivation of an enzyme such as lipoxygenase contained in the seeds such that the generation of a grassy smell can be prevented. Further, such heating results in ease of elution of bitter components peculiar to fenugreek from tissue, and thus a reaction of β-glucosidase in the subsequent step is caused to proceed smoothly. A paste-like product can be obtained by grinding the thus obtained product of fenugreek seeds that have been steamed or boiled with water. Regarding the grinding method, it is convenient to grind a mixture of the above broth and seeds. However, the method is not limited thereto. Grinding is carried out with a food processor, homogenizer, Masscolloider, or the like until a smooth paste-like product is obtained. Thereafter, the temperature is adjusted to approximately 40° C. and the pH of the paste-like product is adjusted with edible acid or alkali to around the optimum pH of β-glucosidase.

The extract extracted from fenugreek seeds is not particularly limited as long as it is obtained by a usual method for extracting an extract, that is, an extraction method using a solvent. Typically, an extract extracted from fenugreek seeds can be obtained by carrying out extraction from a fenugreek seed powder with the use of a solvent and concentrating the obtained extract. The "extract" used in the present invention also includes an extract obtained by adequately diluting a concentrate with a solvent.

A solvent for extraction is hot water, water, a lower alcohol (e.g., methanol or ethanol), a mixture thereof, or the like. Particularly preferably, a liquid mixture of hot water or water and ethanol is used.

When a concentrate (viscous solid product) is used for an enzyme reaction of β-glucosidase, it is preferable to add water thereto. The amount of water added is preferably 1 ml to 100 ml and more preferably 4 ml to 20 ml per each 1 g of the above concentrate (viscous solid product). The use of a concentrate in excessive amounts affects flavor and tends to readily cause formation of a sediment.

3. β-Glucosidase

β-glucosidase used in the present invention is not particularly limited, and it may be derived from a microorganism, plant, or the like. However, preferably, a microorganism-derived β-glucosidase is used in terms of the strength of enzyme activity and substrate compatibility. Examples of a relevant microorganism include *Trichoderma reesei* (*Trichoderma reesei* RUT-C30 (ATCC No. 56765) and *Trichoderma reesei* QM9414 (ATCC No. 26921)). An example of a plant-derived β-glucosidase is almond-derived β-glucosidase.

In addition, examples of β-glucosidase that can be used include not only purified β-glucosidase but also an enzyme preparation containing β-glucosidase. Examples of an enzyme preparation include microorganism-derived Multifect BGL and SPEZYME CP (Genencor Kyowa), and naringinase (Tanabe Seiyaku Co., Ltd.). Multifect BGL and SPEZYME CP (Genencor Kyowa) are liquid enzyme preparations and naringinase is a powdered enzyme preparation. Preferably, such enzyme preparation contains a polysaccharase such as mannanase in addition to β-glucosidase. In addition, it may contain cellulase as a polysaccharase. When fenugreek seeds or materials derived therefrom are treated with β-glucosidase, the viscosity of the reaction mixture increases to a great extent due to the influence of a polysaccharide contained in the fenugreek seeds, which might make it difficult for a reaction of β-glucosidase to proceed. However, with the coexistence of a polysaccharase such as mannanase, the above polysaccharide can be degraded by the polysaccharase. Accordingly, the viscosity of a reaction mixture is maintained at a low level, resulting in the improvement of reaction efficiency and suitability for machine processing upon production.

The amount of β-glucosidase added is not particularly limited. However, when a fenugreek seed powder is used as a reaction raw material and SPEZYME CP is used as an enzyme preparation containing β-glucosidase, it is preferable to first add an adequate amount of water to a powder (20 g) and then add SPEZYME CP (0.001 ml to 20 ml) thereto or to first add SPEZYME CP (0.001 ml to 20 ml) to an adequate amount of water and then add the resultant to a powder (20 g).

Alternatively, when a fenugreek seed powder is used as a reaction raw material and SPEZYME CP is used as an enzyme preparation containing β-glucosidase, it is also possible to first add an adequate amount of water to a powder (1 g) and then add SPEZYME CP (0.001 ml to 20 ml) thereto or to first add SPEZYME CP (0.001 ml to 20 ml) to an adequate amount of water and then add the resultant to a powder (1 g).

In another example, when a paste-like product comprising 20 g of a fenugreek seed powder is used as a reaction raw material and SPEZYME CP is used as an enzyme preparation containing β-glucosidase, it is preferable to add SPEZYME CP (0.001 ml to 20 ml) to the paste-like product.

Alternatively, when a paste-like product comprising 1 g of a fenugreek seed powder is used as a reaction raw material and SPEZYME CP is used as an enzyme preparation containing β-glucosidase, it is possible to add SPEZYME CP (0.001 ml to 20 ml) to the paste-like product.

In another example, when an extract extracted from fenugreek seeds is used as a reaction raw material and SPEZYME CP is used as an enzyme preparation containing β-glucosidase, it is preferable to add SPEZYME CP (0.05 ml to 10 ml) to the extract (1 g) (e.g., an approximately 70-fold concentrate of the extract (a viscous solid product)). In addition, those who carry out the present invention can adequately determine the amount of the enzyme preparation added in accordance with the above examples.

Further, when β-glucosidase is added to a paste-like product prepared with fenugreek seeds, β-glucosidase may be added after the preparation of the paste-like product in the above manner. Alternatively, β-glucosidase may be added to a raw material (i.e., fenugreek seeds, a powder thereof, or water used in the above first method, or fenugreek seeds, a product thereof that has been steamed or boiled, or water used in the above second method) for a paste-like product (prior to the paste forming step), followed by the paste forming step.

4. Enzyme Reaction

The term "enzyme reaction" used in the present invention refers to a reaction caused by β-glucosidase. However, if an enzyme preparation contains polysaccharases such as mannanase and cellulase, the term also refers to reactions caused by such enzymes.

Preferably, an enzyme reaction is carried out within the optimum temperature range and the optimum pH range for an enzyme. The temperature for an enzyme reaction is preferably 20° C. or higher and more preferably 40° C. to 60° C. The reaction time is preferably 48 hours or less and more preferably 2 to 24 hours. When the temperature exceeds 60° C., the activity of β-glucosidase might decrease.

In order to maintain the above reaction temperature, an appropriate warming means can be used. In addition, it is preferable to carry out shaking or agitation rather than allowing a reaction mixture to stand still during enzyme reaction. Accordingly, it becomes possible to uniformly disperse an enzyme for an efficient enzyme reaction and to effectively prevent the generation of a non-uniform mass. Those who carry out the present invention can adequately determine how to carry out the shaking or agitation process.

The pH for an enzyme reaction is preferably adjusted to fall within the optimum pH range by adding edible acid or alkali to a reaction mixture.

5. Enzyme Deactivation

In consideration of the use of the product of the present invention as a food or raw material for food, it is preferable to deactivate an enzyme such as β-glucosidase that has functioned to achieve desired purposes by heating after enzyme reaction. Conditions for deactivation by heating are not particularly limited. However, for example, heating treatment can be carried out at 80° C. to 100° C. for 5 to 10 minutes.

6. Drying/Powder Formation

A mixture subjected to enzyme deactivation can be directly used as the processed product of fenugreek seeds of the present invention. Alternatively, it can be further subjected to drying. For example, drying may be carried out in a manner such that the moisture content is adjusted to 6% by mass or less and preferably 2% to 6% by mass. In addition, a dried product can be adequately pulverized.

The drying method may be a general method involving hot-air drying, spray drying, or the like. However, in terms of flavor, lyophilization is preferable. A lyophilization method can be carried out by a general method.

Examples of a pulverization means used for pulverization include a stamp mill, a Masscolloider, a Comitrol Processor, and a wooden pestle. The particle size of a pulverized product can be adjusted with a sieve according to need.

7. Form of a Processed Product of Fenugreek Seeds

The processed product of fenugreek seeds produced by the method of the present invention is provided in various forms such as a powder, a paste-like product, a highly viscous solid, and an extract of a processed seed product.

8. Use of a Processed Product of Fenugreek Seeds

The processed product of fenugreek seeds of the present invention has α-amylase inhibitory activity that has been enhanced to a greater extent than that of fenugreek seeds or a material derived therefrom used as raw materials. Therefore, the processed product of fenugreek seeds of the present invention can be used as an α-amylase inhibitor.

The processed product of fenugreek seeds of the present invention can be combined with a pharmaceutically acceptable carrier, an additive, an excipient, and the like according to need so as to be used in the form of a pharmaceutical composition having α-amylase inhibitory activity. The administration route of the pharmaceutical composition is not particularly limited, and it is adequately determined according to need. In general, the composition can be administered in the forms of oral preparations such as tablets, capsules, granules, fine granules, powders, liquids, syrups, suspensions, emulsions, and elixirs, or in the forms of parenteral preparations such as injections, infusions, suppositories, agents for inhalation, transdermally absorbable agents, transmucosally absorbable agents, adhesive skin patches, and ointments. A carrier, an additive, an excipient, and the like used for the pharmaceutical composition can be adequately selected depending on the administration route. Examples of diseases that can be treated or prevented with the use of the pharmaceutical composition include diabetes and obesity.

The processed product of fenugreek seeds of the present invention can be used in the form of a food composition having α-amylase inhibitory activity when it is combined with a different material that can be acceptable as a food according to need. The food composition may be labeled as having medicinal effects. For example, it may be labeled as having α-amylase inhibitory activity or reducing blood sugar levels, on a package, a box, a package insert, or an advertising insert, or in the form of electronic information. The form of the food composition is not particularly limited. It may be in various forms such as solid, semi-solid, and liquid forms.

EXAMPLES

The term "fenugreek" used in the following Examples refers to fenugreek seeds, unless otherwise specified.

Enzyme preparations (SPEZYME CP, Multifect BGL, and naringinase) used in the experiments described below include enzymes having their own enzyme activities such as cellulase activity and mannanase activity, in addition to enzymes having the β-glucosidase activity.

Example 1

Method for Producing an Extract Using a Commercially Available SPEZYME CP Enzyme Preparation and Method for Determining α-Amylase-Inhibitory Effects A method for producing an extract and an enzyme treatment of the extract were carried out in the manner described below.

A powder of fenugreek (produced in India) (400 g) was subjected to defatting treatment in diethyl ether (1500 ml) at 85° C. for 3 hours with the use of a Soxhlet extractor, followed by air drying.

The obtained defatted powder (50 g) was subjected to extraction with 30% methanol (500 ml) for 2 hours. The resulting methanol fraction was concentrated such that a yellow-brown solid (7.0 g) was obtained. A liquid obtained by dissolving the solid in a 36 mM (4-morpholino)ethanesulfonic acid (hereinafter abbreviated as MES) aqueous solution was used as an extract in the Examples. The concentration was expressed by the weight of the yellow-brown solid contained in a unit volume of the extract. An extract at a concentration of 0.25 g/ml (200 ul) was mixed with SPEZYME CP (Genencor Kyowa) (35 ul) and 36 mM MES (4765 ul). The mixture was retained at 55° C. for 2 hours such that an enzyme reaction was caused to proceed. After reaction, the mixture was heated at 100° C. for 10 minutes for enzyme deactivation. The enzyme reaction product obtained after deactivation was designated as an enzyme-treated extract (0.01 g/ml after deactivation). Meanwhile, for a control, an extract at a concentration 0.25 g/ml was diluted with MES and the resultant (0.01 g/ml) was used as an untreated extract.

A method for determining α-amylase-inhibitory effects of the extract was carried out in the manner described below.

A substrate solution with a composition comprising 45 mM (4-morpholino)ethanesulfonic acid, 45 mM sodium chloride, 312.5 mM potassium thiocyanate, 1.5 mM calcium acetate, and 0.2 mM 2-chloro-4-nitrophenyl maltotrioside (Oriental Yeast Co., Ltd.) was prepared. In addition, an enzyme solution was prepared by dissolving pig pancreas α-amylase (Sigma) (23 U/mg) in a 36 mM MES solution to a concentration of 0.25 mg/ml. The enzyme solution (10 ul) was added to a solution (100 ul) obtained by mixing an enzyme-treated extract and a 36 mM MES solution in a manner such that the extract concentration upon absorbance measurement was adjusted to 0.5 mg/ml, 1.0 mg/ml, or 1.5 mg/ml, followed by preincubation at 32° C. for 5 minutes. Then, the substrate solution (400 ul) was added thereto, followed by reaction for 2 minutes. Thereafter, the absorbance at 405 nm was determined by a spectrophotometer (Shimadzu Corporation). In addition, a similar experiment was carried out with the use of an untreated extract at the equivalent concentration as a control sample instead of the enzyme-treated extract.

The following equation was used for calculation of the α-amylase inhibition rate: "inhibition rate=(an increase in absorbance in the absence of an extract−an increase in absorbance upon the addition of an extract (an untreated extract or enzyme-treated extract))/an increase in absorbance in the absence of an extract×100 (an increase in absorbance=absorbance in the presence of an enzyme−absorbance in the absence of an enzyme)."

Table 1 and FIG. 1 show the relationship between extract concentrations and inhibition rates. The extract concentration was expressed by the weight of a fenugreek-derived yellow-brown solid contained in a sample used for the final measurement. As a result of SPEZYME treatment, α-amylase-inhibitory effects were enhanced (n=3 for each sample).

TABLE 1

| Fenugreek extract concentration in test solution (mg/ml) | Inhibition rate (%) | | |
|---|---|---|---|
| | Untreated | Enzyme-treated | Increase |
| 0.5 | 37.9 | 43.6 | 5.7 |
| 1 | 61.4 | 81.8 | 20.4 |
| 1.5 | 73.0 | 90.4 | 17.4 |

Example 2

Determination of α-Amylase-Inhibitory Effects of an Extract Produced with the Use of Fractionated β-Glucosidase A DE52 ion-exchange resin (OH⁻ type) equilibrated with 5 mM phosphate buffer (pH 7.0) (approximately 16 g) was loaded into a column (10 mm×200 mm). Then, SPEZYME CP (1 ml, corresponding to 72 mg in terms of the protein amount) was applied to the column. 5 mM phosphate buffer (pH 7.0) was used for development such that 110 fractions (0.5 ml (2.5 min) each) were obtained. Fractions 10 to 40 were collected and a fraction lacking cellulase activity and having β-glucosidase activity was obtained. An extract (0.25 g/ml) (40 ul) obtained as in Example 1 was mixed with the β-glucosidase fraction (140 ul) obtained by fractionation and a 36 mM MES solution (820 ul), followed by an enzyme treatment operation as in Example 1. Determination of α-amylase-inhibitory effects was carried out as in Example 1.

Figure 2:
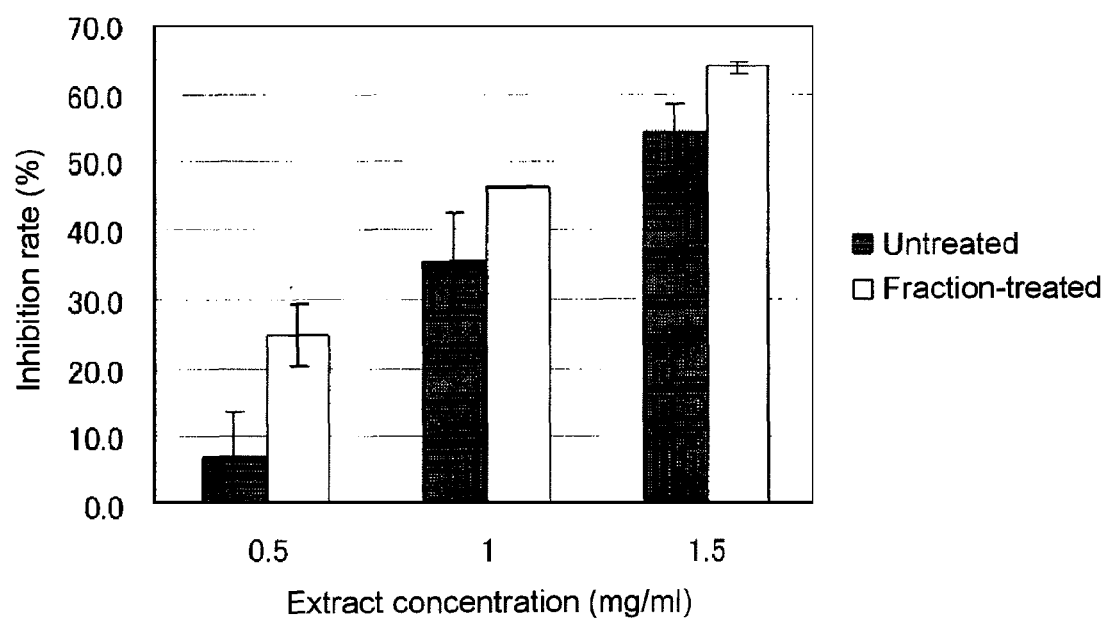
FIG. 2 is a chart showing the relationship between concentrations of extracts extracted from fenugreek seeds treated with β-glucosidase fractionated from SPEZYME CP and α-amylase activity inhibition rates.

Table 2 and FIG. 2 show the relationship between extract concentrations and inhibition rates. As a result of treatment with the β-glucosidase active fraction fractionated from SPEZYME CP, the inhibitory effects were enhanced to an extent comparable to those in the case involving treatment with SPEZYME CP.

TABLE 2

| Fenugreek extract concentration in test solution (mg/ml) | Inhibition rate (%) | |
|---|---|---|
| | Untreated | Fraction-treated |
| 0.5 | 6.9 | 24.7 |
| 1 | 35.5 | 46.3 |
| 1.5 | 54.3 | 64.0 |

Example 3

Determination of α-Amylase-Inhibitory Effects of an Extract Produced with the Use of β-Glucosidase (Almond)

An extract (0.25 g/ml) (40 ul) obtained as in Example 1 was mixed with almond-derived β-glucosidase (Oriental Yeast Co., Ltd.) (37 U/mg) (0.1 mg) and a 36 mM MES solution (860 ul). The mixture was maintained at 37° C. for 4 days such that the enzyme reaction was caused to proceed. After reaction, the mixture was heated at 100° C. for 10 minutes for enzyme deactivation. Then, determination of α-amylase-inhibitory effects was carried out as in Example 1.

Figure 3:
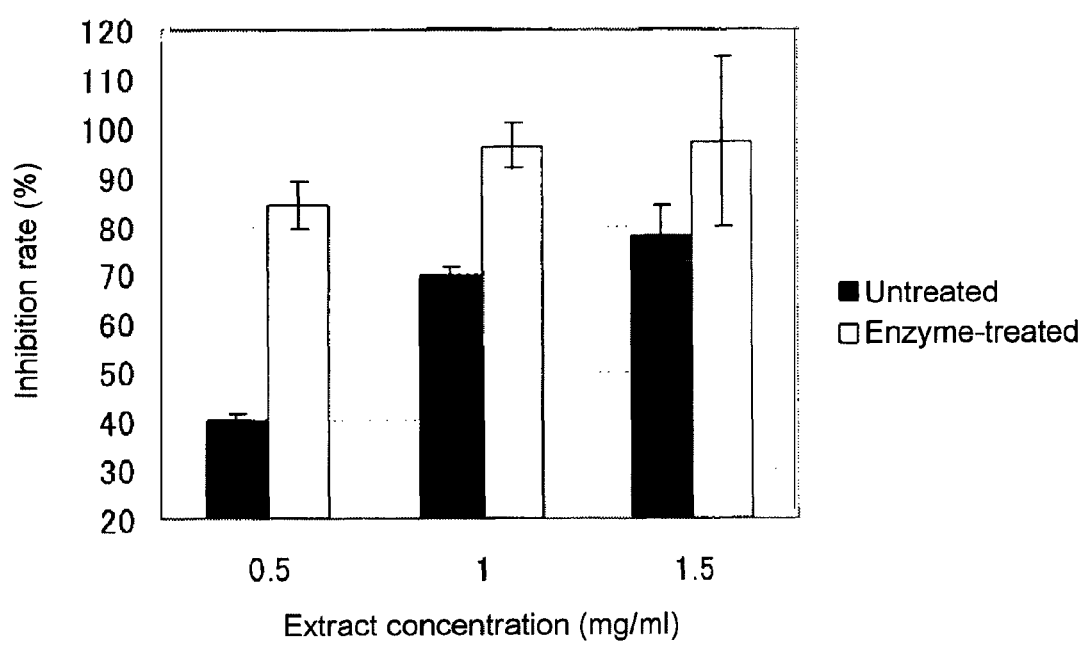
FIG. 3 is a chart showing the relationship between concentrations of extracts extracted from fenugreek seeds treated with almond-derived β-glucosidase and α-amylase activity inhibition rates.

Table 3 and FIG. 3 show the relationship between extract concentrations and inhibition rates. As a result of treatment with the β-glucosidase active fraction, the inhibitory effects were enhanced to an extent comparable to or greater than those in the case involving treatment with SPEZYME CP.

TABLE 3

| Fenugreek extract concentration in test solution (mg/ml) | Inhibition rate (%) | | |
|---|---|---|---|
| | Untreated | Enzyme-treated | Increase |
| 0.5 | 40.1 | 84.2 | 44.1 |
| 1 | 69.6 | 96.2 | 26.6 |
| 1.5 | 78.1 | 97.1 | 19.0 |

Example 4

Determination of α-Amylase-Inhibitory Effects of an Enzyme-Treated Powder

Enzyme treatment of a fenugreek powder was carried out in the manner described below.

Water (115 g) was added to a fenugreek powder (20 g), followed by mixing. Thus, a paste-like product was obtained. The pH of the paste-like product was adjusted to 5.0 with hydrochloric acid. SPEZYME CP (Genencor Kyowa) (1.9 ml) was added thereto, followed by incubation at 55° C. for 6 hours for enzyme reaction. After reaction, deactivation treatment was carried out at 100° C. for 10 minutes. Then, the paste-like product was cooled, lyophilized, and pulverized so as to be formed into a powder. Thus, a fenugreek powder treated with SPEZYME CP was obtained.

The reagent used for determination of α-amylase-inhibitory effects of the powder was the same as in Example 1. A 36 mM MES solution (200 ul) was mixed with an enzyme solution (20 ul). The fenugreek powder treated with SPEZYME CP (10 mg) was added thereto, followed by mixing in a sufficient manner and preincubation at 37° C. for 5 minutes. Then, a substrate solution (800 ul) was added thereto for reaction for 5 minutes. After reaction, the resultant was boiled for 10 minutes for discontinuation of enzyme reaction, followed by centrifugation at 13000 rpm for 10 minutes. Then, the supernatant was obtained. The supernatant was allowed to pass through a 0.45 um filter and injected into HPLC (Shimadzu Corporation; column: PEGASIL ODS-2, 4.6φ×250 mm (Senshu Scientific co., ltd.); mobile phase: a solution obtained by mixing methanol and 31.25 mM phosphate buffer (pH 6.79) at a ratio of 2:8; and flow rate: 0.5 ml/min), followed by absorbance measurement at 405 nm. The peak observed at a retention time of approximately 13.2 minutes was derived from a product obtained by enzyme reaction. The inhibition rate was calculated based on the peak area ratio (table 4): inhibition rate=(peak area in the absence of a powder−peak area obtained with the addition of a powder)/peak area in the absence of a powder×100.

Figure 4:
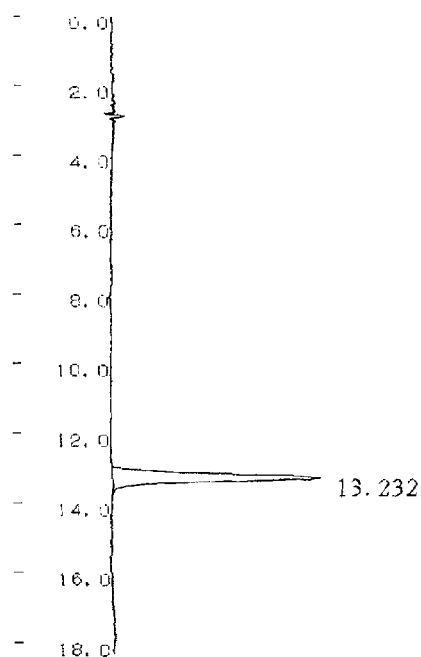
FIG. 4 is a typical HPLC chart obtained in Example 4.
Figure 5:
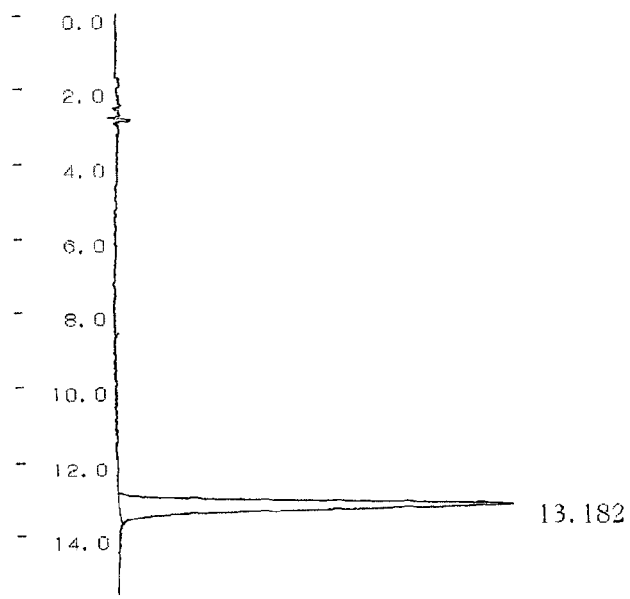
FIG. 5 is a typical HPLC chart obtained in Example 4.
Figure 6:
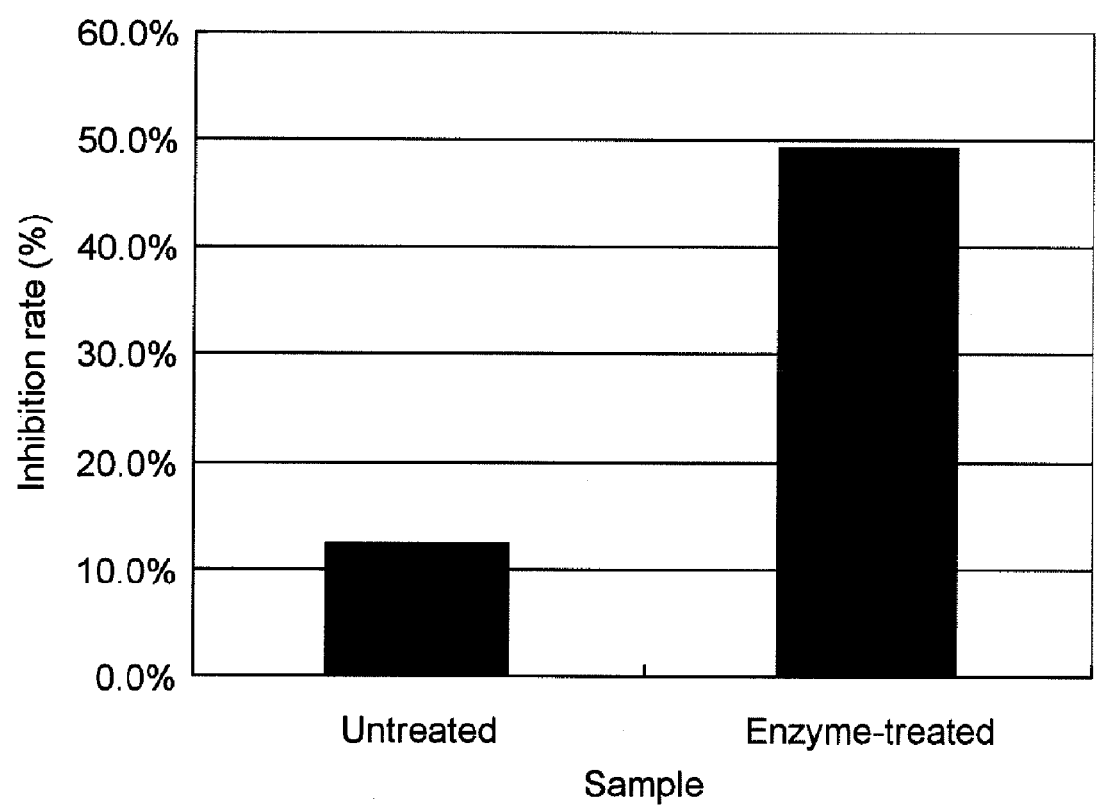
FIG. 6 is a chart showing the relationship between implementation or non-implementation of treatment of a fenugreek seed powder with SPEZYME CP and α-amylase activity inhibition rates.

FIGS. 4 and 5 show typical charts. FIG. 6 shows the relationship between treatment method and inhibition rates (n=2 for each sample).

TABLE 4

| Sample | Experiment 1 | Experiment 2 | Average | Inhibition rate |
|---|---|---|---|---|
| Enzyme-free | 49887 | 55256 | 52571.5 | — |
| Untreated | 50491 | 41480 | 45985.5 | 12.5% |
| Enzyme-treated | 26879 | 26368 | 26623.5 | 49.4% |

Example 5

Determination of the Degree of Bitter Taste of Seeds and Amount of 4-OH-isoleucine Water was weighed at 130 to 180 g, poured into a pan, and boiled. Then, fenugreek seeds (produced in India) (20 g) were added thereto and heated in boiling water for 1 to 5 minutes. Thereafter, water was added thereto so that the total amount of the mixture became 135 g. After the addition of water, 1M HCl (2 ml) was added thereto, followed by grinding at 9,000 rpm for 1 minute with an Excel Auto Homogenizer (Nippon Seiki Co., Ltd.). After 1 minute, grinding was discontinued. SPEZYME CP (Genencor Kyowa) (1.9 ml) was added thereto, followed by more grinding at 9,000 rpm for 4 minutes. The paste-like product obtained by grinding was introduced into a 50-ml centrifuge tube, followed by incubation in a thermostatic water bath at 55° C. for 3 to 9 hours. After incubation, the product was heated in boiling water for 2 minutes for deactivation of SPEZYME CP, followed by cooling. Then, the pH of the product was adjusted to become approximately neutral. The thus obtained paste-like product treated with SPEZYME CP was subjected to sensory evaluation. (Rating was carried out in a manner such that the bitter taste of the control was rated as 10 and the absence of bitter taste was rated as 0, that 10 panelists were randomly selected, and that the order of effects was considered upon sensory evaluation.) As a control sample, a paste-like product obtained by a similar form of treatment (except that no SPEZYME CP was added thereto) was used. As a result of sensory tests, 10 out of 10 panelists judged that the bitter taste was reduced. A significant difference was found via a pair test at a critical rate of 0.1%. Table 5 shows the results.

For determination of 4-OH-isoleucine, a test solution was obtained by lyophilizing the paste-like product treated above and carrying out extraction with 70% ethanol, and the solution was analyzed with an amino acid analyzer (Shimadzu Corporation). As a control sample, a test solution obtained by pulverizing fenugreek seeds and carrying out extraction in 70% ethanol was used. Table 6 shows the results. One-way analysis of variance was carried out based on the amount of 4-OH-isoleucine in each treated sample. As a result, no significant difference was found at a critical rate of 5%. Accordingly, the treated product was found to have excellent flavor and maintain other components, such as 4-OH-isoleucine, without any change.

TABLE 5

Bitterness intensity of enzyme-treated sample (control score: 10)

| Panelist | 1-minute heating | Panelist | 2-minute heating | Panelist | 5-minute heating |
|---|---|---|---|---|---|
| 1-1-A | 7 | 1-2-A | 6 | 1-5-A | 4 |
| 1-1-B | 3 | 1-2-B | 2 | 1-5-B | 4 |
| 1-1-C | 0.5 | 1-2-C | 1 | 1-5-C | 8 |
| 1-1-D | 5 | 1-2-D | 4 | 1-5-D | 3 |
| 1-1-E | 1 | 1-2-E | 3 | 1-5-E | 0.1 |
| 1-1-F | 2 | 1-2-F | 0 | 1-5-F | 1 |
| 1-1-G | 2 | 1-2-G | 4 | 1-5-G | 4 |
| 1-1-H | 0 | 1-2-H | 1 | 1-5-H | 5 |
| 1-1-I | 0 | 1-2-I | 0.5 | 1-5-I | 1 |
| 1-1-J | 3 | 1-2-J | 2 | 1-5-J | 2 |

TABLE 6

Analyzed value of 4-OH-isoleucine content in 1 g of fenugreek (peak area)

| Sample | Mean value | 95% confidence interval | Raw data 1 | Raw data 2 |
|---|---|---|---|---|
| Seed (control) | 4.93E+07 | 8.28E+07 | 5.58E+07 | 4.28E+07 |
| 1-minute heating | 4.31E+07 | 1.31E+07 | 4.42E+07 | 4.21E+07 |
| 5-minute heating | 4.24E+07 | 5.50E+06 | 4.20E+07 | 4.28E+07 |
| 0-minute heating | 4.60E+07 | 1.02E+07 | 4.68E+07 | 4.52E+07 |

Example 6

α-Amylase-Inhibitory Effects of a Paste Treated with a SPEZYME CP Enzyme Preparation Fenugreek seeds (20 g) were added to boiling water (180 g), followed by heating for 5 minutes and then cooling. Water was added to the resultant so that the total amount of the mixture became 135 g. 1M hydrochloric acid (2.7 ml) was added thereto, followed by treatment with a homogenizer at 9000 rpm for 5 minutes. Thus, a paste with a pH of 5.0 was obtained.

Next, two samples of the above paste (30 g) were prepared. A SPEZYME CP enzyme preparation (422 µl) was added to one of the samples, followed by mixing. An enzyme-free sample was obtained by adding water (422 µl) to the other sample (paste product: 30 g), followed by mixing. The two obtained samples were incubated at 55° C. for 6 hours and heated at 90° C. for 15 minutes for deactivation of the enzyme contained in the enzyme-treated sample. Thereafter, each sample was cooled to room temperature with the use of water and adjusted to a pH of 7.0, followed by lyophilization under conditions of freezing at −80° C. and drying in an atmosphere at a 9 Pa degree of vacuum for 64 hours. Then, each resultant was pulverized so as to be formed into a powder.

The α-amylase inhibitory activity of each of the two obtained powders was determined. Determination was carried out in the manner described below.

A substrate solution obtained as in Example 1 was used, except that the calcium acetate concentration was 4.5 mM. A 36 mM MES solution (200 d) and the fenugreek powder treated with SPEZYME CP (10 mg) were added to and lightly mixed with the substrate solution. An enzyme solution obtained as in Example 1 (20 µl) was added thereto and lightly mixed therewith, followed by incubation at 37° C. for 5 minutes. Then, the α-amylase inhibitory activity was determined by the method used in Example 4, except that the α-amylase reaction time was 10 minutes (37° C.). Table 7 lists the results. The effects of α-amylase inhibitory activity in the sample treated with the SPEZYME CP enzyme preparation were enhanced to a level at least twice as great as those in the sample not treated with the SPEZYME CP enzyme preparation.

TABLE 7

|  | Inhibition rate (%) | Standard deviation (n = 2) |
| --- | --- | --- |
| Enzyme-treated sample | 68.4 | 0.85 |
| Non-enzyme-treated sample | 33.3 | 10.21 |

Example 7

α-Amylase-Inhibitory Effects of a Paste Treated with Almond-Derived β-Glucosidase Fenugreek seeds (20 g) were added to boiling water (180 g), followed by heating for 5 minutes and then cooling. Water was added to the resultant so that the total amount of the mixture became 135 g. 1M hydrochloric acid (2.6 ml) was added thereto, followed by treatment with a homogenizer at 9000 rpm for 5 minutes. Thus, a paste with a pH of 5.3 was obtained.

Next, two samples of the above paste (10 g) were prepared. A mixture of almond-derived β-glucosidase (30 mg) and distilled water (500 µl) was added to one of the samples, followed by reaction at 37° C. for 48 hours. Then, heating was carried out at 90° C. for 15 minutes for deactivation of the enzyme contained in the enzyme-treated sample. Thereafter, each sample was cooled to room temperature with the use of water and adjusted to a pH of 7.0, followed by lyophilization under conditions of freezing at −80° C. and drying in an atmosphere at a 9 Pa degree of vacuum for 64 hours. Then, each resultant was pulverized so as to be formed into a powder.

The α-amylase inhibitory activity of each of the two obtained powders was determined. The α-amylase inhibitory activity was determined by the method used in Example 6. Table 8 lists the results. The effects of α-amylase inhibitory activity in the sample treated with almond-derived β-glucosidase were enhanced to a level at least twice as great as those in the sample not treated with the enzyme.

TABLE 8

|  | Inhibition rate (%) | Standard deviation (n = 2) |
| --- | --- | --- |
| Enzyme-treated sample | 70.5 | 1.81 |
| Non-enzyme-treated sample | 33.3 | 10.21 |

Example 8

α-Amylase-Inhibitor Effects of a Paste Treated with a SPEZYME CP Enzyme Preparation Fenugreek seeds were pulverized by a roll mill such that a powder of approximately 60 mesh pass was obtained. Water (57.5 g) was added to and mixed with the obtained fenugreek powder of approximately 60 mesh pass (10 g) such that a paste product was obtained. Next, two samples of the paste product (25 g) were prepared. A SPEZYME CP enzyme preparation (826 µl) was added to one of the samples, followed by mixing. An enzyme-free sample was obtained by adding water (826 µl) to the other sample (paste product: 25 g), followed by mixing.

The two obtained samples were incubated at 55° C. for 24 hours and heated at 90° C. for 15 minutes for deactivation of the enzyme contained in the enzyme-treated sample. Thereafter, lyophilization was carried out under conditions of freezing at −80° C. and drying in an atmosphere at a 9 Pa degree of vacuum for 64 hours. Then, each resultant was pulverized so as to be formed into a powder. The α-amylase inhibitory activity of each of the two obtained powders was determined. The α-amylase inhibitory activity was determined by the method used in Example 6. Table 9 lists the results. The effects of α-amylase inhibitory activity in the sample treated with the SPEZYME CP enzyme preparation were enhanced to a level greater than those in the sample not treated with the SPEZYME CP enzyme preparation.

TABLE 9

|  | Inhibition rate (%) | Standard deviation (n = 2) |
| --- | --- | --- |
| Enzyme-treated sample | 63.7 | 0.20 |
| Non-enzyme-treated sample | 43.1 | 1.98 |

Example 9

α-Amylase-Inhibitory Effects of a Paste Treated with a SPEZYME CP Enzyme Preparation A fenugreek powder of approximately 60 mesh pass (20 g) obtained by pulverizing fenugreek seeds with a roll mill was added to boiling water (180 g), followed by heating for 5 minutes. Water was added to the resultant so that the total amount of the mixture became 135 g. Next, two samples of the obtained paste (25 g) were prepared. A SPEZYME CP enzyme preparation (826 µl) was added to one of the samples, followed by mixing. An enzyme-free sample was obtained by adding water (826 µl) to the other sample (paste product: 25 g), followed by mixing.

The two obtained samples were incubated at 55° C. for 24 hours and heated at 90° C. for 15 minutes for deactivation of the enzyme contained in the enzyme-treated sample. Thereafter, lyophilization was carried out under conditions of freezing at −80° C. and drying in an atmosphere at a 9 Pa degree of vacuum for 64 hours. Then, each resultant was pulverized and formed into a powder. The α-amylase inhibitory activity of each of the two obtained powders was determined. The α-amylase inhibitory activity was determined by the method used in Example 6. Table 10 lists the results. The effects of α-amylase inhibitory activity in the sample treated with the SPEZYME CP enzyme preparation were enhanced to a level greater than those in the sample not treated with the SPEZYME CP enzyme preparation.

TABLE 10

|  | Inhibition rate (%) | Standard deviation (n = 2) |
| --- | --- | --- |
| Enzyme-treated sample | 65.7 | 0.88 |
| Non-enzyme-treated sample | 55.9 | 0.15 |

Example 10

The Enzyme Concentration and α-Amylase-Inhibitory Effects

Fenugreek seeds (20 g) were added to boiling water (180 g), followed by heating for 5 minutes and then cooling. Water was added to the resultant so that the total amount of the mixture became 135 g. 1M hydrochloric acid (2.6 ml) was added thereto, followed by treatment with a homogenizer at 9000 rpm for 5 minutes. Thus, a paste with a pH of 4.8 was obtained. The above treatment was repeated twice. The obtained paste was divided into separate portions (40 g each). Then, 4 samples containing the SPEZYME CP enzyme preparation at concentrations of 1 μl, 10 μl, 100 μl, and 20 ml per each 20 g of fenugreek seeds were prepared. That is, when the concentration of the SPEZYME CP enzyme preparation was 1 μl, 22 μl of a 100-fold diluted solution of the SPEZYME CP enzyme preparation was added to 40 g of the paste. When the concentration of the SPEZYME CP enzyme preparation was 10 μl, 222 μl of a 100-fold diluted solution of the SPEZYME CP enzyme preparation was added to 40 g of the paste. When the concentration of the SPEZYME CP enzyme preparation was 100 μl, 222 μl of a 10-fold diluted solution of the SPEZYME CP enzyme preparation was added to 40 g of the paste. When the concentration of the SPEZYME CP enzyme preparation was 20 ml, 4.4 ml of the SPEZYME CP enzyme preparation was added to 40 g of the paste.

The obtained 4 samples were incubated at 55° C. for 10 days and heated at 90° C. for 15 minutes for deactivation of the enzyme contained in the enzyme-treated sample. Thereafter, lyophilization was carried out under conditions of freezing at −80° C. and drying in an atmosphere at a 9 Pa degree of vacuum for 64 hours. Then, each resultant was pulverized so as to be formed into a powder. The α-amylase inhibitory activity of each of the two obtained powders was determined. The α-amylase inhibitory activity was determined by the method used in Example 6. Table 11 lists the results. Regarding the effects of α-amylase inhibitory activity, the enzyme-treated samples were superior to the non-enzyme-treated sample in terms of α-amylase inhibitory activity. In addition, the sample containing the SPEZYME CP enzyme preparation at a concentration of 1 μl was most excellent.

TABLE 11

|  | Inhibition rate (%) | Standard deviation (n = 2) |
| --- | --- | --- |
| Treated sample: 1 ul | 73.4 | 3.09 |
| Treated sample: 10 ul | 68.7 | 1.39 |
| Treated sample: 100 ul | 64.7 | 1.08 |
| Treated sample: 20 ml | 68.2 | 2.01 |
| Non-enzyme-treated sample | 50.3 | 4.79 |

Example 11

α-Amylase-Inhibitor Effects in the Case of Paste Obtained with the Addition of Water in a 1-Fold Amount Relative to the Amount of Fenugreek Seeds Water (25 g) was added to a fenugreek powder of approximately 60 mesh pass (25 g) obtained by pulverizing fenugreek seeds with a roll mill, followed by mixing. The obtained paste was divided into two portions (20 g each). A SPEZYME CP enzyme preparation (2.85 ml) was added to one of the samples, followed by mixing by agitation. Water (2.85 ml) was added to the other sample, followed by mixing. Then, the two obtained samples were incubated at 55° C. for 24 hours and heated at 90° C. for 15 minutes for enzyme deactivation. Thereafter, lyophilization was carried out under conditions of freezing at −80° C. and drying in an atmosphere at a 9 Pa degree of vacuum for 64 hours. Then, each resultant was pulverized so as to be formed into a powder. Accordingly, the enzyme-treated product was obtained with the addition of water in a 1-fold amount relative to the amount of fenugreek seeds.

The α-amylase inhibitory activity of each of the two obtained powders was determined. The α-amylase inhibitory activity was determined by the method used in Example 6. Table 12 lists the results. The effects of α-amylase inhibitory activity in the sample treated with the SPEZYME CP enzyme preparation were enhanced to a level greater than those in the sample not treated with the SPEZYME CP enzyme preparation.

TABLE 12

|  | Inhibition rate (%) | Standard deviation (n = 2) |
| --- | --- | --- |
| Enzyme-treated sample | 63.5 | 1.62 |
| Non-enzyme-treated sample | 58.4 | 2.94 |

Example 12

α-Amylase-Inhibitory Effects in the Case of a Paste Obtained with the Addition of Water in a 20-Fold Amount Relative to the Amount of Fenugreek Seeds The method used in Example 11 was carried out under similar conditions except for the differences in conditions described below. Water (200 g) was added to a fenugreek powder of approximately 60 mesh pass (10 g) obtained by pulverizing fenugreek seeds with a roll mill, followed by mixing by agitation. The obtained paste was divided into two portions (100 g each). A SPEZYME CP enzyme preparation (2.26 ml) was added to one of the samples and water (2.26 ml) was added to the other sample. Table 13 lists the results. The effects of α-amylase inhibitory activity in the sample treated with the SPEZYME CP enzyme preparation were enhanced to a level greater than those in the sample not treated with the SPEZYME CP enzyme preparation.

TABLE 13

| | Inhibition rate (%) | Standard deviation (n = 2) |
|---|---|---|
| Enzyme-treated sample | 53.4 | 3.37 |
| Non-enzyme-treated sample | 43.1 | 1.98 |

Example 13

α-Amylase-Inhibitory Effects in Cases Involving the Addition of Boiling Water in 9-Fold and 3-Fold Amounts Relative to the Amount of Fenugreek Seeds Fenugreek seeds (20 g) were added to boiling water (180 g) and boiled therein for 5 minutes, followed by cooling. Water was added to the resultant so that the total amount of the mixture became 135 g. 1M hydrochloric acid (2.6 ml) was added thereto. The resultant was pulverized with a homogenizer at 9000 rpm for 5 minutes such that a paste with a pH of 4.9 was obtained. Then, the obtained paste was divided into separate portions (30 g each). A SPEZYME CP enzyme preparation (422 µl) was added to one of the samples and distilled water (422 µl) was added to the other sample, followed by mixing. The sample to which the enzyme preparation had been added was designated as a treated sample. The sample to which distilled water had been added was designated as an untreated sample. Then, the two obtained samples were incubated at 55° C. for 22.5 hours and heated at 90° C. for 15 minutes for enzyme deactivation. Thereafter, each sample was cooled to room temperature with the use of water and adjusted to a pH of 7.0, followed by lyophilization under conditions of freezing at −80° C. and drying in an atmosphere at a 9 Pa degree of vacuum for 64 hours. Then, each resultant was pulverized so as to be formed into a powder.

The α-amylase inhibitory activity of each of the two obtained powders was determined. The α-amylase inhibitory activity was determined by the method used in Example 6.

In addition, the method used in the case involving the addition of boiling water in a 9-fold amount relative to the amount of fenugreek seeds was carried out under similar conditions except for the differences in conditions described below. Fenugreek seeds (20 g) were added to boiling water (60 g) and boiled therein for 5 minutes, followed by cooling. Water was added to the resultant so that the total amount of the mixture became 80 g. The resultant was pulverized such that a paste-like product with a pH of 5.0 was obtained. Then, a SPEZYME CP enzyme preparation (712.5 µl) was added to the paste (30 g), followed by mixing. Table 14 lists the results. The effects of α-amylase inhibitory activity in the sample treated with the SPEZYME CP enzyme preparation with the addition of water in a 9-fold amount relative to the amount of the seeds were enhanced to a level greater than those in the sample treated with the SPEZYME CP enzyme preparation with the addition of water in a 3-fold amount relative to the amount of the seeds. However, in both cases, the effects were enhanced to a level greater than those in the sample not treated with a SPEZYME CP enzyme preparation.

TABLE 14

| | Inhibition rate (%) | Standard deviation (n = 2) |
|---|---|---|
| Enzyme-treated sample (3-fold amount of water) | 71.4 | 2.95 |
| Enzyme-treated sample (9-fold amount of water) | 75.5 | 2.64 |
| Non-enzyme-treated sample | 45.1 | 1.09 |

Example 14

α-Amylase-Inhibitory Effects Obtained with the Addition of a SPEZYME CP Enzyme Preparation Upon Grinding of Fenugreek Seeds Fenugreek seeds (1 kg) were boiled in boiling water (5.75 kg) for 5 minutes, followed by cooling. Water was added to the resultant so that the total amount of the mixture became 6.75 kg. A SPEZYME CP enzyme preparation (95 g) was added thereto, sufficiently agitated therewith, and immersed therein for 20 minutes. Then, the resultant was pulverized with a Masscolloider (Masuko Sangyo Co., Ltd.) (clearance: 300 µm) and adjusted to a pH of 5.0 with 12 M hydrochloric acid. Thus, a paste-like product was obtained. Thereafter, the obtained paste was placed in an inclined reactor and incubated at 55° C. for 8 hours, followed by heating at 90° C. for 15 minutes for enzyme deactivation. Then, the resultant was cooled to room temperature with the use of water and adjusted to a pH of 7.0, followed by lyophilization under conditions of freezing at −80° C. and drying in an atmosphere at a 9 Pa degree of vacuum for 64 hours. Then, the resultant was pulverized so as to be formed into a powder. Meanwhile, fenugreek seeds were pulverized with a roll mill such that a powder of approximately 60 mesh pass was obtained as an non-enzyme-treated product.

The α-amylase inhibitory activity of each of the two obtained powders was determined. The α-amylase inhibitory activity was determined by the method used in Example 6. Table 15 lists the results. The effects of α-amylase inhibitory activity in the sample treated with the SPEZYME CP enzyme preparation were enhanced to a level greater than those in the sample not treated with the SPEZYME CP enzyme preparation.

TABLE 15

| | Inhibition rate (%) | Standard deviation (n = 2) |
|---|---|---|
| Enzyme-treated sample | 72.0 | 1.96 |
| Non-enzyme-treated sample | 56.2 | 3.37 |

Example 15

α-Amylase-Inhibitory Effects of an Extract Extracted with Hot Water

Two samples of an extract (25 g) extracted with hot water from fenugreek seeds at 95° C. for 15 minutes were prepared. A SPEZYME CP enzyme preparation (275 µl) was added to one of the samples, followed by mixing. Distilled water (275 µl) was added to the other sample, followed by mixing. Then, each sample was incubated at 55° C. for 24 hours and heated at 90° C. for 15 minutes for enzyme deactivation. The α-amylase inhibitory activity of each of the two obtained samples of the extract extracted with hot water was determined. The determination method is described below.

A substrate solution obtained as in Example 6 was used. The extract (200 mg) extracted with hot water and the fenugreek powder (10 mg) treated with a SPEZYME CP enzyme preparation were lightly mixed with the substrate solution. Then, an enzyme solution (20 ul) obtained as in Example 1 was added thereto and lightly agitated therein, followed by preincubation at 37° C. for 5 minutes. Thereafter, the α-amylase inhibitory activity was determined by the method used in Example 6.

Table 16 lists the results. The effects of α-amylase inhibitory activity in the sample treated with the SPEZYME CP enzyme preparation were enhanced to a level greater than those in the sample not treated with the SPEZYME CP enzyme preparation.

TABLE 16

|  | Inhibition rate (%) | Standard deviation (n = 2) |
| --- | --- | --- |
| Enzyme-treated sample | 71.5 | 0.3 |
| Non-enzyme-treated sample | 67.3 | 0.3 |

Example 16

α-Amylase-Inhibitory Effects Obtained with the Use of Naringinase

A defatted powder (50 g) was subjected to extraction with 30% methanol (500 ml) for 2 hours. The obtained methanol fraction was concentrated such that a yellow-brown solid (7.0 g) was obtained. Then, a liquid obtained by dissolving the obtained solid in a 36 mM (4-morpholino)ethanesulfonic acid (hereinafter abbreviated as MES) aqueous solution was designated as an extract. The concentration was expressed by the weight of the yellow-brown solid contained in a unit volume of the extract. The extract (concentration: 0.25 g/ml) (200 ul) was mixed with naringinase (Tanabe Seiyaku Co., Ltd.) (100 mg/ml, 1.8 ml) and 36 mM MES (3 ml). The mixture was retained at 70° C. for 12 hours such that an enzyme reaction was caused to proceed. After reaction, the mixture was heated at 100° C. for 10 minutes for enzyme deactivation. The enzyme reaction product obtained after deactivation was designated as an enzyme-treated extract (0.01 g/ml after deactivation). Meanwhile, an extract at a concentration 0.25 g/ml was diluted with MES and the resultant (0.01 g/ml) was designated as an untreated extract to be used as a control sample.

The method used in Example 1 was used as a method for determining α-amylase-inhibitory effects of the extract. Table 17 lists the results. The effects of α-amylase inhibitory activity in the sample treated with the enzyme (naringinase) were enhanced to a level greater than those in the sample not treated with the enzyme (naringinase).

TABLE 17

|  | Inhibition rate (%) | Standard deviation (n = 3) |
| --- | --- | --- |
| Enzyme-treated sample | 53.2 | 2.13 |
| Non-enzyme-treated sample | 46.8 | 2.84 |

Example 17

α-Amylase-Inhibitory Effects of Germinated Fenugreek

Water (53.1 g) and a SPEZYME CP enzyme preparation (1.9 ml) were added to fenugreek seeds (20 g). The resultant was allowed to stand in a thermostatic bath at 25° C. for 48 hours and then removed from the bath. Then, only germinated seeds were separated therefrom and water (20 ml) was added to the germinated seeds. Further, a portion of the remaining immersion solution was collected in an amount calculated by the following formula: the total amount of remaining immersion solution (ml)×the amount of germinated seeds obtained by sampling (g)/the total amount of seeds (g). The germinated seeds and the previously mentioned portion of the solution were mixed together and subjected to pulverization treatment with a homogenizer (Nippon Seiki Co., Ltd.) at 9000 rpm for 5 minutes, followed by heating at 100° C. for 10 minutes for enzyme deactivation. Lyophilization was carried out under conditions of freezing at −80° C. and drying in an atmosphere at a 9 Pa degree of vacuum for 64 hours. Then, the resultant was pulverized so as to be formed into a powder. Meanwhile, fenugreek seeds were pulverized with a roll mill such that a powder of approximately 60 mesh pass was obtained as an untreated product.

The α-amylase inhibitory activity of each obtained powder was determined. Determination was carried out by the method used in Example 6. Table 18 lists the results. The effects of α-amylase inhibitory activity were also enhanced in the case of the germinated fenugreek powder treated with the SPEZYME CP enzyme preparation.

TABLE 18

|  | Inhibition rate (%) | Standard deviation (n = 2) |
| --- | --- | --- |
| Enzyme-treated sample | 51.0 | 1.19 |
| Non-enzyme-treated sample | 43.1 | 1.98 |

Example 18

Method for Determining α-Amylase Inhibitory Effects of an Extract Obtained with the Use of a SPEZYME CP Enzyme Preparation A method for producing an extract and enzyme treatment of the extract were carried out in the manner described below.

A powder of approximately 60 mesh pass (400 g) obtained by pulverizing fenugreek seeds (produced in India) with a roll mill was subjected to defatting treatment in diethyl ether (1500 ml) at 85° C. for 3 hours with the use of a Soxhlet extractor, followed by air drying.

The obtained defatted powder (50 g) was subjected to extraction with 30% methanol (500 ml) for 2 hours. The obtained methanol fraction was concentrated such that a yellow-brown solid (7.0 g) was obtained. Then, a liquid obtained by dissolving the obtained solid in a 36 mM (4-morpholino) ethanesulfonic acid (hereinafter abbreviated as MES) aqueous solution was designated as an extract. The concentration was expressed by the weight of the yellow-brown solid contained in a unit volume of the extract. The extract (concentration: 0.25 g/ml) (200 ul) was mixed with SPEZYME CP (Genencor Kyowa) (35 ul) and 36 mM MES (4765 ul). The mixture was retained at 55° C. for 2 hours such that an enzyme reaction was caused to proceed. After reaction, the mixture was heated at 100° C. for 10 minutes for enzyme deactivation. The enzyme reaction product obtained after deactivation was designated as an enzyme-treated extract (0.01 g/ml after deactivation). Meanwhile, for a control, an extract at a concentration of 0.25 g/ml was diluted with MES and the resultant (0.01 g/ml) was used as an untreated extract.

A method for determining α-amylase-inhibitory effects of an extract was carried out in the manner described below.

A substrate solution with a composition comprising 45 mM (4-morpholino)ethanesulfonic acid, 45 mM sodium chloride, 312.5 mM potassium thiocyanate, 1.5 mM calcium acetate, and 0.2 mM 2-chloro-4-nitrophenyl maltotrioside (Oriental Yeast Co., Ltd.) was prepared. In addition, an enzyme solution was prepared by dissolving pig pancreas α-amylase (Sigma) (23 U/mg) in a 36 mM MES solution to a concentration of 0.25 mg/ml. A solution (100 ul) was obtained by mixing an enzyme-treated extract and a 36 mM MES solution such that the extract concentration upon absorbance measurement was adjusted to 0.5 mg/ml, 1.0 mg/ml, or 1.5 mg/ml. An enzyme solution (10 ul) was added thereto, followed by preincubation at 37° C. for 5 minutes. Then, the substrate solution (400 ul) was added thereto, followed by reaction at 32° C. for 2 minutes. Thereafter, the absorbance at 405 nm was determined by a spectrophotometer (Shimadzu Corporation). In addition, an untreated extract at the equivalent concentration was used as a control instead of the enzyme-treated extract and a similar experiment was carried out.

The following equation was used for calculation of the α-amylase inhibition rate: "inhibition rate=(an increase in absorbance in the absence of an extract–an increase in absorbance upon the addition of an extract (an untreated extract or enzyme-treated extract))/an increase in absorbance in the absence of an extract×100 (an increase in absorbance=absorbance in the presence of an enzyme–absorbance in the absence of an enzyme)."

Figure 7:
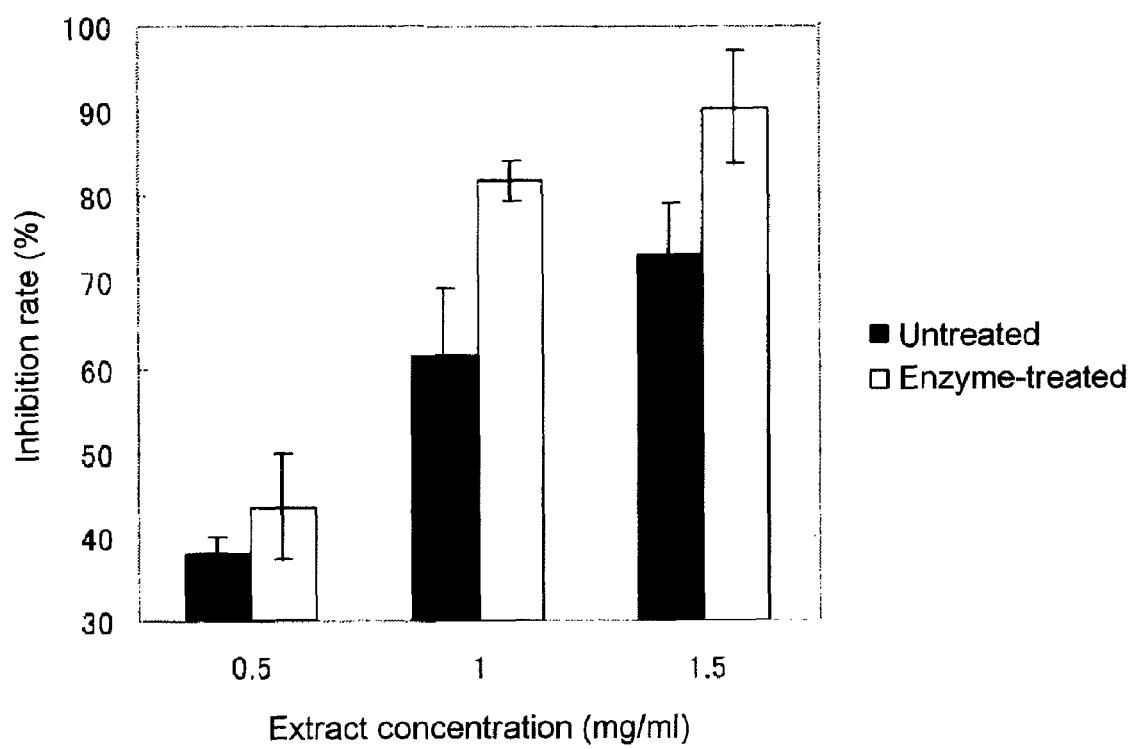
FIG. 7 is a chart showing the relationship between concentrations of extracts extracted from fenugreek seeds treated with SPEZYME CP and α-amylase activity inhibition rates.

Table 19 and FIG. 7 show the relationship between extract concentrations and inhibition rates. The extract concentration was expressed by the weight of a fenugreek-derived yellow-brown solid contained in a sample for the final measurement. As a result of SPEZYME treatment, α-amylase-inhibitory effects were enhanced (n=3 for each sample).

TABLE 19

| Fenugreek extract concentration in test solution (mg/ml) | Inhibition rate (%) | | |
| --- | --- | --- | --- |
| | Untreated | Enzyme-treated | Increase |
| 0.5 | 37.9 | 43.6 | 5.7 |
| 1 | 61.4 | 81.8 | 20.4 |
| 1.5 | 73.0 | 90.4 | 17.4 |

Example 19

Determination of α-Amylase-Inhibitory Effects of an Extract Produced with the Use of Fractionated β-Glucosidase A DE52 (OH⁻ type) ion-exchange resin equilibrated with 5 mM phosphate buffer (pH 7.0) (approximately 16 g) was loaded into a column (10 mm×200 mm). Then, SPEZYME CP (1 ml, corresponding to 72 mg in terms of the protein amount) was applied to the column. 5 mM phosphate buffer (pH 7.0) was used for development such that 110 fractions (0.5 ml (2.5 min) each) were obtained. Fractions 10 to 40 were collected and a fraction lacking cellulase activity and having β-glucosidase activity was obtained. An extract (0.25 g/ml) (40 ul) obtained as in Example 18 was mixed with the β-glucosidase fraction (140 ul) obtained by fractionation and a 36 mM MES solution (820 ul), followed by an enzyme treatment operation as in Example 18. A method for determining the α-amylase-inhibitory effects of the extract was carried out in the manner described below.

A substrate solution with a composition comprising 45 mM (4-morpholino)ethanesulfonic acid, 45 mM sodium chloride, 312.5 mM potassium thiocyanate, 4.5 mM calcium acetate, and 2 mM 2-chloro-4-nitrophenyl maltotrioside (Oriental Yeast Co., Ltd.) was prepared. In addition, an enzyme solution was prepared by dissolving pig pancreas α-amylase (Sigma) (23 U/mg) in a 36 mM MES solution to a concentration of 0.25 mg/ml. The enzyme solution (10 ul) was added to a solution (100 ul) obtained by mixing an enzyme-treated extract and a 36 mM MES solution in a manner such that the extract concentration upon absorbance measurement was adjusted to 0.5 mg/ml, 1.0 mg/ml, or 1.5 mg/ml, followed by preincubation at 37° C. for 5 minutes. Then, the substrate solution (400 ul) was added thereto, followed by reaction at 37° C. for 5 minutes. Thereafter, the absorbance at 405 nm was determined by a spectrophotometer (Shimadzu Corporation). In addition, a similar experiment was carried out with the use of an untreated extract at the equivalent concentration as a control sample instead of the enzyme-treated extract.

Figure 8:
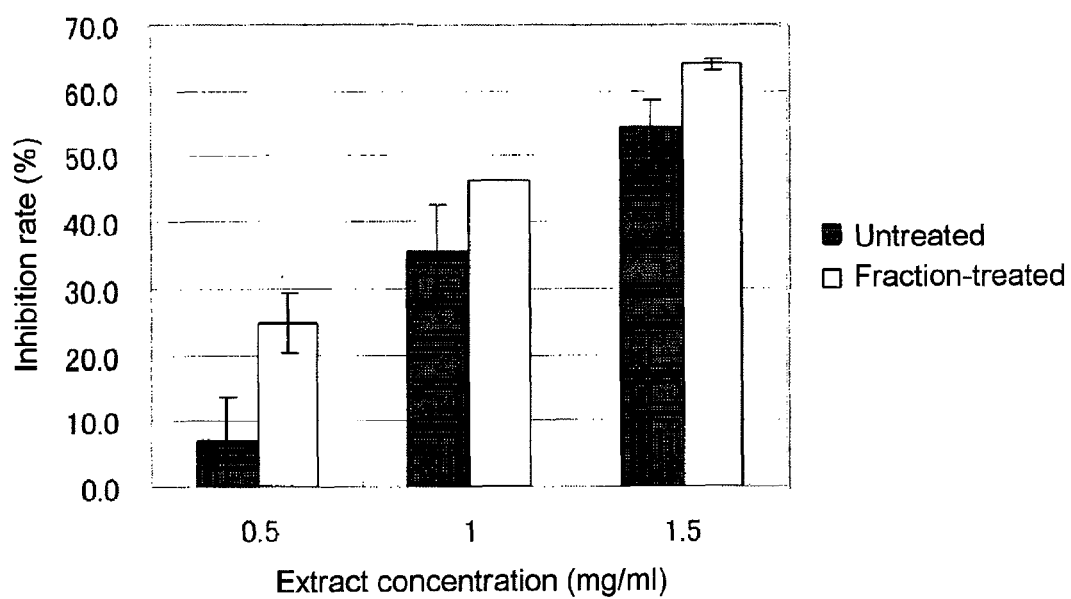
FIG. 8 is a chart showing the relationship between concentrations of extracts extracted from fenugreek seeds treated with β-glucosidase fractionated from SPEZYME CP and α-amylase activity inhibition rates.

Table 20 and FIG. 8 show the relationship between extract concentrations and inhibition rates. As a result of treatment with the β-glucosidase active fraction fractionated from SPEZYME CP, the inhibitory effects were enhanced to an extent comparable to the case involving treatment with SPEZYME CP.

TABLE 20

| Fenugreek extract concentration | Inhibition rate (%) | |
| --- | --- | --- |
| in test solution (mg/ml) | Untreated | Enzyme-treated |
| 0.5 | 6.9 | 24.7 |
| 1 | 35.5 | 46.3 |
| 1.5 | 54.3 | 64.0 |

Example 20

Determination of α-Amylase-Inhibitory Effects of an Extract Treated with β-Glucosidase (Almond)

An extract (40 ul, 0.25 g/ml) obtained as in Example 18 was mixed with almond-derived β-glucosidase (Oriental Yeast Co., Ltd.) (0.1 mg, 37 U/mg) and a 36 mM MES solution (860 ul). The mixture was retained at 37° C. for 4 days such that an enzyme reaction was caused to proceed. After reaction, the mixture was heated at 100° C. for 10 minutes for enzyme deactivation. Then, determination of α-amylase-inhibitory effects was carried out as in Example 18.

Figure 9:
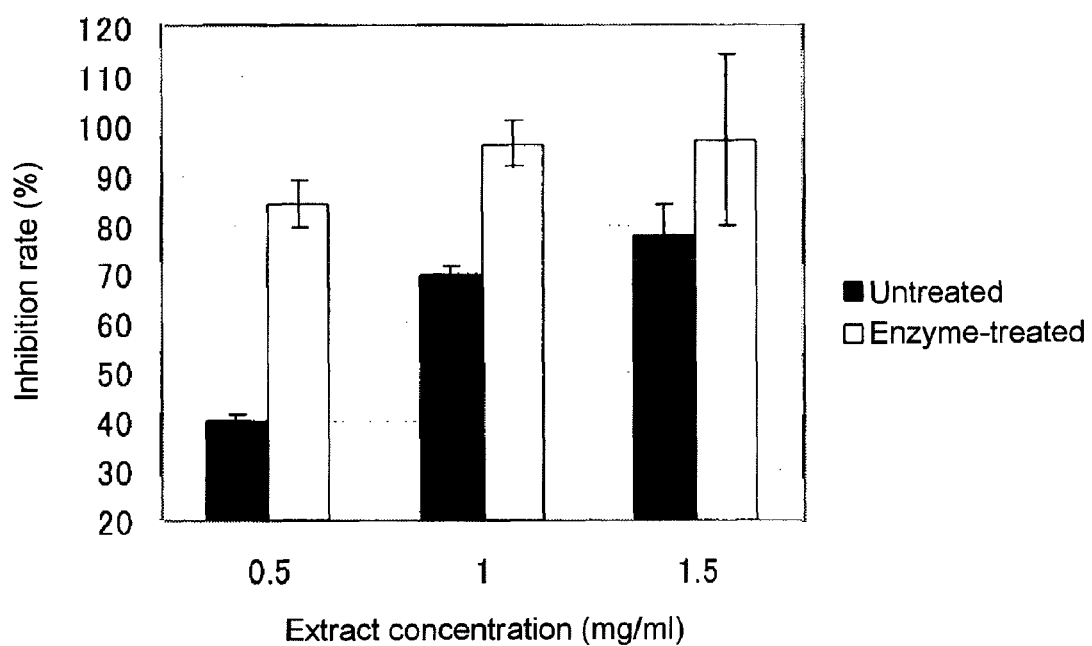
FIG. 9 is a chart showing the relationship between concentrations of extracts extracted from fenugreek seeds treated with almond-derived β-glucosidase and α-amylase activity inhibition rates.

Table 21 and FIG. 9 show the relationship between extract concentrations and inhibition rates. As a result of treatment with the β-glucosidase active fraction, the inhibitory effects were enhanced to an extent comparable to or greater than those in the case involving treatment with SPEZYME CP.

TABLE 21

| Fenugreek extract concentration in test solution (mg/ml) | Inhibition rate (%) | | |
|---|---|---|---|
| | Untreated | Enzyme-treated | Increase |
| 0.5 | 40.1 | 84.2 | 44.1 |
| 1 | 69.6 | 96.2 | 26.6 |
| 1.5 | 78.1 | 97.1 | 19.0 |

Example 21

Determination of α-Amylase-Inhibitory Effects of an Enzyme-Treated Powder

Enzyme treatment of a fenugreek powder was carried out in the manner described below.

Water (115 g) was added to a fenugreek powder (20 g), followed by mixing. Thus, a paste-like product was obtained. The pH of the paste-like product was adjusted to 5.0 with hydrochloric acid. SPEZYME CP (Genencor Kyowa) (1.9 ml) was added thereto, followed by incubation at 55° C. for 6 hours for enzyme reaction. After reaction, deactivation treatment was carried out at 100° C. for 10 minutes. Then, the paste-like product was cooled, followed by lyophilization under conditions of freezing at −80° C. and drying in an atmosphere at a 9 Pa degree of vacuum for 64 hours. The resultant was pulverized so as to be formed into a powder. Thus, a fenugreek powder treated with SPEZYME CP was obtained.

For determination of the α-amylase-inhibitory effects of the powder, a substrate solution to be used was prepared as in Example 18 except that the calcium acetate concentration was 4.5 mM and the 2-chloro-4-nitrophenyl maltotrioside concentration was 2 mM. A 36 mM MES solution (200 ul) was mixed with an enzyme solution (20 ul). The fenugreek powder treated with SPEZYME CP (10 mg) was added thereto and lightly agitated therewith, followed by preincubation at 37° C. for 5 minutes. Thereafter, the substrate solution (800 ul) was added thereto and lightly agitated therewith for reaction for 5 minutes. After reaction, the resultant was boiled for 10 minutes for discontinuation of enzyme reaction, followed by centrifugation at 13000 rpm for 10 minutes. Then, the supernatant was obtained. The supernatant was allowed to pass through a 0.45 um filter and injected into HPLC (Shimadzu Corporation; column: PEGASIL ODS-2, 4.6φ×250 mm (Senshu Scientific co., ltd.); mobile phase: a solution obtained by mixing methanol and 31.25 mM phosphate buffer (pH 6.79) at a ratio of 2:8; and flow rate: 1.0 ml/min), followed by absorbance measurement at 405 nm. The peak observed at a retention time of approximately 13.2 minutes was derived from a product obtained by enzyme reaction. The inhibition rate was calculated based on the peak area ratio (table 22) inhibition rate=(peak area in the absence of a powder−peak area obtained with the addition of a powder)/peak area in the absence of a powder×100.

Figure 10:
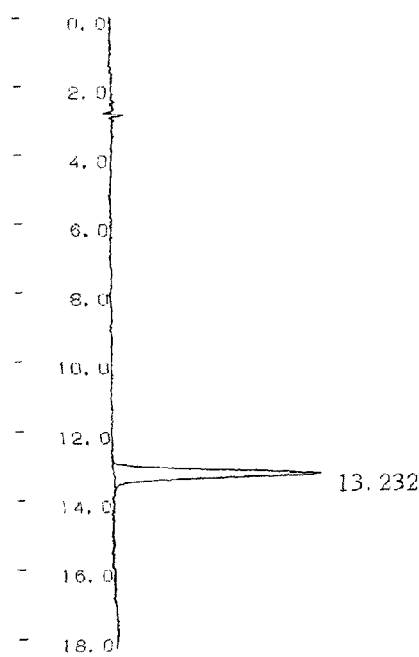
FIG. 10 is a typical HPLC chart obtained in Example 21.
Figure 11:
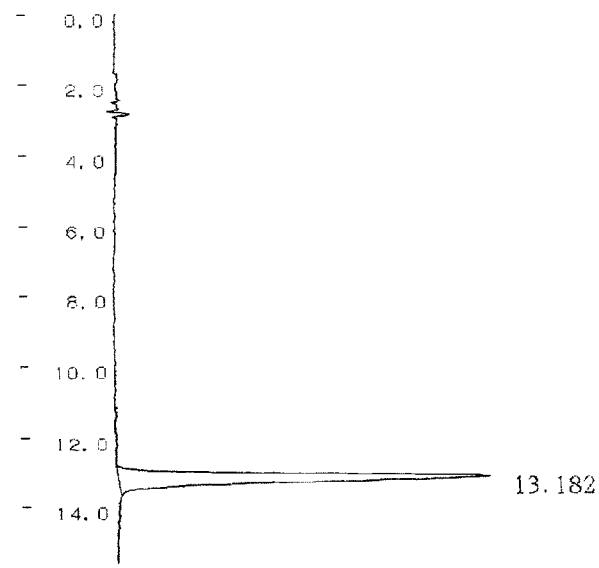
FIG. 11 is a typical HPLC chart obtained in Example 21.
Figure 12:
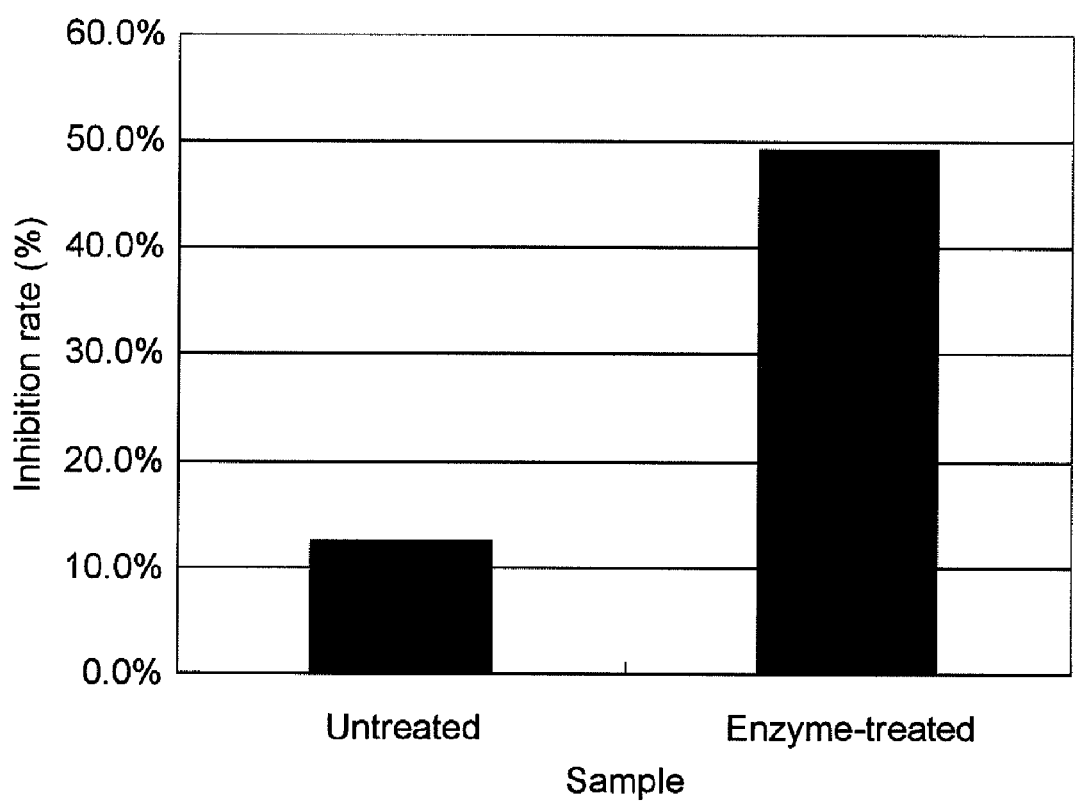
FIG. 12 is a chart showing the relationship between implementation or non-implementation of treatment of a fenugreek seed powder with SPEZYME CP and α-amylase activity inhibition rates.

FIGS. 10 and 11 show typical charts. FIG. 12 shows the relationship between treatment method and inhibition rates (n=2 for each sample).

TABLE 22

| Sample | Experiment 1 | Experiment 2 | Average | Inhibition rate |
|---|---|---|---|---|
| Enzyme-free | 49887 | 55256 | 52571.5 | — |
| Untreated | 50491 | 41480 | 45985.5 | 12.5% |
| Enzyme-treated | 26879 | 26368 | 26623.5 | 49.4% |

Reference Example

Each of the moisture contents of fenugreek seeds and fenugreek seed powders used in Example 1 to 21 was 10% by mass.

All publications, patents, and patent applications cited herein are incorporated herein by reference in their entirety.

The invention claimed is:

1. A method for producing a processed product of fenugreek seeds, consisting essentially of the following steps:
    an extraction step of obtaining an extract from powdered fenugreek seeds by extraction using a solvent;
    an enzyme addition step of adding β-glucosidase to the extract and mixing the resultant;
    an enzyme reaction step of causing an enzyme reaction to proceed in the mixture obtained in the enzyme addition step at 40° C. to 60° C. for 2 to 24 hours;
    optionally a drying step; and
    optionally a deactivation step of deactivating the enzyme after the enzyme reaction step.

2. The method according to claim 1, wherein an enzyme preparation containing β-glucosidase is used as the β-glucosidase.

3. The method according to claim 1, wherein the deactivation step comprises a heating treatment carried out at 80° C. to 100° C. for 5 to 10 minutes.

4. A method for producing a processed product of fenugreek seeds, consisting of the following steps:
    an extraction step of obtaining an extract from powdered fenugreek seeds of by extraction using a solvent;
    an enzyme addition step of adding β-glucosidase to the extract and mixing the resultant;
    an enzyme reaction step of causing an enzyme reaction to proceed in the mixture obtained in the enzyme addition step at 40° C. to 60° C. for 2 to 24 hours;
    optionally a drying step; and
    optionally a deactivation step of deactivating the enzyme after the enzyme reaction step.

* * * * *